United States Patent [19]

Del Bono

[11] 4,378,358
[45] Mar. 29, 1983

[54] BENZOTHIAZINOPYRAZOLES HAVING PHARMACOLOGICAL ACTIVITY

[75] Inventor: Rinaldo Del Bono, Milan, Italy

[73] Assignee: Mediolanum Farmaceutici s.r.l., Milan, Italy

[21] Appl. No.: 279,455

[22] Filed: Jul. 1, 1981

[30] Foreign Application Priority Data

Jul. 14, 1980 [IT] Italy ............................ 23418 A/80
Jun. 18, 1981 [IT] Italy ............................ 22405 A/81

[51] Int. Cl.³ .................. C07D 513/04; A61K 31/54
[52] U.S. Cl. ................................ 424/246; 544/33
[58] Field of Search ..................... 544/33; 424/246

[56] References Cited

U.S. PATENT DOCUMENTS 3,346,572 10/1967 Shavel et al. ................... 544/33
3,925,371 12/1975 Rasmussen ...................... 544/49

*Primary Examiner*—John M. Ford
*Attorney, Agent, or Firm*—Bucknam and Archer

[57] ABSTRACT

1,2 Benzothiazino[3,4-d]pyrazoles of the following general formula

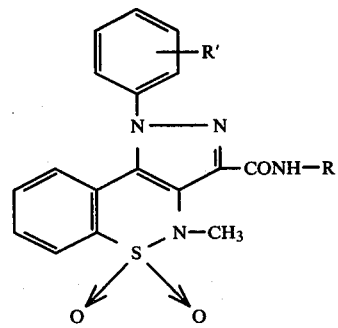

wherein R stands for a linear or branched ($C_{2-4}$) alkyl chain bearing a substituent of formula

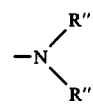

in which the R" radicals may be the same or different and represent hydrogen, ($C_{2-4}$)alkyl, ($C_{4-7}$) cycloalkyl or, taken together with the adjacent nitrogen atom, may also represent a saturated, 5 to 7 membered heterocyclic ring containing from one to three heteroatoms independently selected from O, N and S, or R may represent the 1-ethyl-pyrrolidine-2-yl-methyl radical, and R' is hydrogen, a halogen atom or a ($C_{1-4}$) alkyl radical; methods for their preparation; pharmaceutical compositions containing them. The compounds possess antiinflammatory, antipyretic and analgesic activity.

29 Claims, No Drawings

BENZOTHIAZINOPYRAZOLES HAVING PHARMACOLOGICAL ACTIVITY

The present invention refers to 1,2-benzothiazino[3,4-d]pyrroles of the following general formula

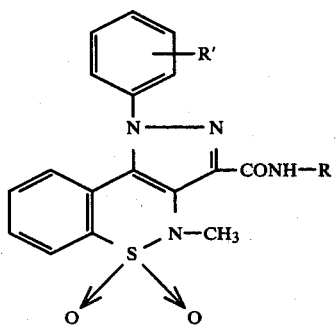

wherein R stands for a linear or branched ($C_{2-4}$)alkyl chain bearing a substituent of formula

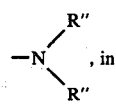

which the R" radicals may be the same or different and represent hydrogen, ($C_{1-4}$)alkyl, ($C_{4-7}$)cycloalkyl or, taken together with the adjacent nitrogen atom, may also represent a saturated, 5 to 7 membered heterocyclic ring containing from one to three hetero atoms independently selected from O, N and S or R may represent the 1-ethyl-pyrrolidine-2-yl-methyl-radical, and R' is hydrogen, a halogen atom or a ($C_{1-4}$)alkyl radical.

The compounds possess antiinflammatory, antipyretic and analgesic utility.

Preferred meanings for the R radical are 2-dimethylaminoethyl, 2-diethylaminoethyl, 3-dimethylaminopropyl, 3-diethylaminopropyl, 3-morpholinopropyl, 3-cyclohexylaminopropyl and 1-ethylpyrrolidine-2-ylmethyl. Preferred meanings for the R' radical are chloro and bromo.

The compounds according to the invention can be prepared starting from 2-methyl-4-oxo-1,2-benzothiazine-S,S-dioxide of formula II (see below), which, in turn, is prepared according to literature methods (Zinnes et al., J. Org. Chem., 31, 162, 1966). Compound II is reacted with a dialkyl oxalate, preferably dimethyl oxalate, in the presence of a base such as, for instance, an alkali alkoxide, preferably sodium methoxide, in order to obtain the corresponding (2-methyl-4-oxo-1,2-benzothiazine-3-yl)-glyoxylic acid methyl ester, S,S-dioxide of formula III (see below). This compound is reacted with predetermined phenylhydrazines, whereby the desired 1,2-benzothiazinopyrroles of formula IV (see below) are obtained, wherein R' is as above defined.

The condensation with the phenylhydrazines is carried out in alcoholic solution, preferably in a methanolic solution, at the boiling temperature of the reaction solvent until complete reaction (2–4 hours). The so obtained esters of formula IV are used for preparing the end compounds of formula I above by reaction with predetermined amines of formula V

R—NH$_2$  V wherein R has the meanings given before. This reaction step is carried out in the absence of solvents, by employing a molar excess of the amine compound of general formula V, at the reflux temperature of the reaction mixture. Alternatively, the esters of formula IV can be hydrolized to the corresponding acids which in turn can be transformed into the desired amides of formula I via previous formation of the corresponding acyl halides or mixed anhydrides.

The various reaction steps are illustrated in the following scheme:

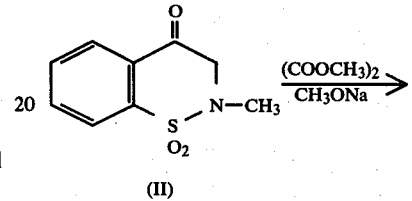

(II)

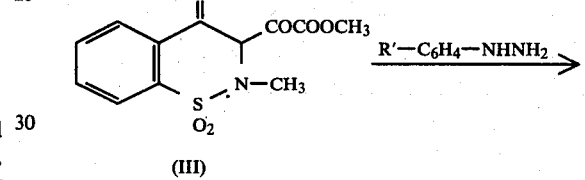

(III)

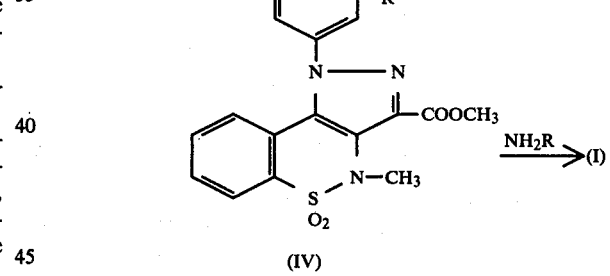

(IV)

The compounds of the invention are then isolated and purified according to usual techniques.

The compounds of formula I prepared according to the present invention are listed in the following Table

TABLE

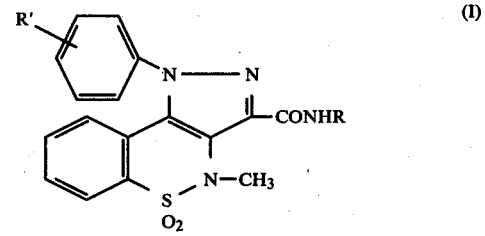

(I)

| Compound | R | R' | M.p. °C. | Cryst. Solvent |
|---|---|---|---|---|
| I-1 | A | H | 180–82 | EtOH |
| I-2 | B | H | 147–48 | AcOEt |
| I-3 | C | H | 187–89 | AcOEt |
| I-4* | D | H | 158–60 | EtOH |
| I-5 | A | p-CH$_3$ | 197–99 | MeOH |
| I-6 | B | p-CH$_3$ | 152–54 | cyclohexane/AcOEt |

TABLE-continued

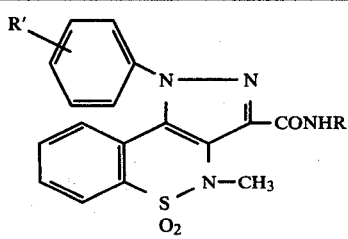

(I)

| Compound | R | R' | M.p. °C. | Cryst. Solvent |
|---|---|---|---|---|
| I-7 | C | p-CH₃ | 154–56 | MeOH |
| I-8 | D | p-CH₃ | 119–21 | EtOH |
| I-9 | A | o-Cl | 207–09 | EtOH |
| I-10 | B | o-Cl | 185–87 | EtOH |
| I-11 | C | o-Cl | 245–47 | DMF |
| I-12 | D | o-Cl | 142–44 | hexane/AcOEt |
| I-13 | A | m-Cl | 143–45 | hexane/AcOEt |
| I-14 | B | m-Cl | 169–71 | EtOH |
| I-15 | C | m-Cl | 191–93 | EtOH |
| I-16 | D | m-Cl | 133–35 | ligroine |
| I-17 | A | p-Cl | 208–10 | EtOH |
| I-18 | C | p-Cl | 159–61 | EtOH |
| I-19 | D | p-Cl | 138–40 | EtOH |
| I-20 | A | m-F | 158–60 | hexane/AcOEt |
| I-21 | B | m-F | 143–45 | hexane/AcOEt |
| I-22 | C | m-F | 163–65 | hexane/AcOEt |
| I-23* | D | m-F | 104–106 | hexane/AcOEt |
| I-24* | E | H | 128–29 | hexane/AcOEt |
| I-25* | B | p-Cl | 188–90 | EtOH |

A = —(CH₂)₂—N(Et)₂
B = —(CH₂)₃—N(CH₃)₂

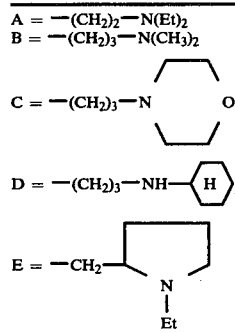

In the following there are reported the spectroscopical characteristics of the compounds of the previous table marked with an asterisk. The N.M.R.-spectra are recorded with a 90 MHz apparatus in CDCl₃, using TMS (tetramethylsilane) as the internal standard. The position of the resonance peaks is expressed as δ values (p.p.m.=parts per million). The I.R.-spectra are recorded in nujol. The absorption frequencies are expressed in cm⁻¹.

| N.M.R.-spectra δ (p.p.m.) | I.R.-spectra cm⁻¹ | |
|---|---|---|
| Compound I-4 | | |
| 1,00–2,00 δ (m, 13H, C—CH₂—C + —⟨H⟩) | 3200 | NH |
| 2,40 δ (b, 1H, NH) | 1660 | —CO |
| 2,82 δ (t, 2H, CH₂—N) | 1355 | SO₂ |
| 3,45 δ (s, 3H, N—CH₃) | | |
| 3,50–3,70 δ (m, 2H, COHN—CH₂—C) | | |
| 6,92–8,06 δ (m, 9H, aromatici) | | |
| 8,38 δ (b, 1H, CO—NH) | | |
| I-23 | | |
| 1-2 δ (m, 13H, C—CH₂—C + —⟨H⟩) | 3210 | —NH |
| 2,45 δ (b, 1H, NH) | 3090 | —NH |
| 2,87 δ (t, 2H, CH₂—NH) | 1660 | —CO |
| 3,45 δ (s, 3H, N—CH₃) | 1365 | —SO₂ |
| 3,50–3,70 δ (m, 2H, C—CH₂—NHCO) | | |
| 7,00–8,10 δ (m, 8H, aromatici) | | |
| 8,50 δ (b, 1H, NH—C=O) | | |
| I-24 | | |
| 1,12 δ (t, 3H, CH₂CH₃) | 3350 | —NH |
| 1,60–3,85 δ (m, 11H, alif. + 1H NH) | 1668 | —CO |
| 3,45 δ (s, 3H, N—CH₃) | 1350 | —SO₂ |
| 6,90–8,10 δ (m, 9H, aromatici) | | |
| I-25 | | |
| 0,90–3,60 δ (m, 6H, 3CH₂) | | |
| 2,20 δ (s, 6H, 2CH₃) | | |
| 3,40 δ (s, 3H, CH₃) | | |
| 7,00–8,00 δ (m, 8H, aromatici). | | | s = singlet;
t = triplet;
m = multiplet;
b = broad

The following examples are provided only with the purpose of better illustrating the invention, but in no way they must be construed as a limitation of the invention itself.

EXAMPLE 1

(2-Methyl-4-oxo-1,2-benzothiazine-3-yl)-glyoxylic acid methyl ester, S,S-dioxide (III)

A solution of 1.2 grams (0.01 mole) of dimethyl oxalate and 0.01 mole of sodium methoxide in 30 ml of anhydrous benzene was added dropwise under nitrogen atmosphere with a solution of 2.20 g (0.01 mole) 2-methyl-4-oxo-1,2-benzothiazine-S,S-dioxide (II) in anhydrous benzene. The reaction mixture was stirred at room temperature under nitrogen atmosphere for 4 hours, then the formed precipitate was collected and washed with benzene. The so obtained sodium salt was dissolved in water, the so obtained solution was acidified, whereby a crystalline yellow precipitate separated. Yield: 42% of the title compound. M.p.: 142°–44° C. (from methanol).

EXAMPLE 2

2-Methyl-5-phenyl-1,2-benzothiazino[3,4-d]pyrazole-3-yl-carboxylic acid methyl ester, S,S-dioxide (IV-1)

A solution of 2.96 g (0.01 mole) of the compound of Example 1 in 40 ml of methanol was added with 1.90 g (0.013 mole) of phenylhydrazine hydrochloride. The reaction mixture was refluxed for 4 hours then, after cooling, the title product began to separate. The so obtained precipitate was crystallized from methanol. Yield: 82%. M.p.: 188°–89° C.

Following substantially the same procedure but using, instead of phenylhydrazine, a suitable substituted phenylhydrazine, the following compounds were prepared:

(a) 2-methyl-5-(4-methylphenyl)-1,2-benzothiazino[3,4-d]pyrazole-3-yl-carboxylic acid methyl ester,S,S,-dioxide (IV-2), from 4-methyl-phenylhydrazine; m.p.: 239°–41° C. (from acetic acid);

(b) 5-(2-chlorophenyl)-2-methyl-1,2-benzothiazino[3,4-d]pyrazole-3-yl-carboxylic acid methyl ester,S,S-dioxide (IV-3), from 2-chloro-phenylhydrazine; m.p.: 182°–84° C. (from ethanol);

(c) 5-(3-chlorophenyl)-2-methyl-1,2-benzothiazino[3,4-d]pyrazole-3-yl-carboxylic acid methyl ester,S,S,-dioxide (IV-4), from 3-chloro-phenylhydrazine; m.p.: 245°–46° C. (from acetic acid);

(d) 5-(4-chlorophenyl)-2-methyl-1,2-benzothiazino[3,4-d]pyrazole-3-yl-carboxylic acid methylester,S,S-dioxide (IV-5), from 4-chloro-phenylhydrazine; m.p.: 220°–22° C. (from methanol);

(e) 5-(3-fluorophenyl)-2-methyl-1,2-benzothiazino[3,4-d]pyrazole-3-yl-carboxylic acid methylester,S,S-dioxide (IV-6)- from 3-fluoro-phenylhydrazine; m.p.: 216°–19° C. (from ethanol).

EXAMPLE 3

2-methyl-5-phenyl-1,2-benzothiazino[3,4-d]pyrazole-3-yl-carboxylic acid,
2-(N,N-diethylamino)ethylamide,S,S-dioxide (I-1).

A mixture of 1.0 g of the compound of Example 2 and 3.0 g (0.026 mole) of 1-amino-2-diethylamino-ethane was refluxed for 2 hours; after cooling and diluting with water, a white crystalline product separated which was re-crystallized from ethanol. M.p.: 180°–82° C. By operating substantially as described in the foregoing example and condensing the various esters IV-1,2,3,4,5,6 with the suitable amine compounds, the end amides of formula I listed in the Table were obtained. The toxicological and pharmaceutical properties of some representative compounds of formula I are hereinbelow reported taking into consideration, as the comparison substances, piroxicam and naproxen, i.e. two well-known and widely used antiinflammatory, antipyretic and analgesic drugs.

Acute toxicity, per os

| Animals: 5 female mice per dose, average body weight: 25g  5 female rats per dose, average body weight: 150g | | | | |
|---|---|---|---|---|
| Compound | Animal | LD 50: mg/kg (Litchfield and Wilcoxon) | Relative ratio to Piroxicam | Naproxen |
| Piroxicam | Mouse | 360[a] | 1 | — |
|  | Rat | 270[a] | 1 | — |
| Naproxen | Mouse | 1234[b] | — | 1 |
|  | Rat | 543[b] | — | 1 |
| I-1 | Mouse | 2850 | 7.9 | 2.3 |
|  | Rat | 2700 | 10.0 | 5.0 |
| I-2 | Mouse | 1380 | 3.8 | 1.1 |
|  | Rat | 2400 | 8.9 | 4.4 |
| I-3 | Mouse | 2200 | 6.1 | 1.8 |
|  | Rat | 1080 | 4.0 | 2.0 |
| I-4 | Mouse | 720 | 2.0 | 0.6 |
|  | Rat | 1090 | 4.0 | 2.0 |
| I-20 | Mouse | 1600 | 4.4 | 1.3 |
|  | Rat | 2220 | 8.2 | 4.1 |
| I-21 | Mouse | 1520 | 4.2 | 1.2 |
|  | Rat | 2260 | 8.4 | 4.2 |
| I-23 | Mouse | 720 | 2.0 | 0.6 |
|  | Rat | 1200 | 4.4 | 2.2 |
| I-24 | Mouse | 760 | 2.1 | 0.6 |
|  | Rat | 1060 | 3.9 | 2.0 |

[a]WISEMAN et al. - Piroxicam; Proceedings of the Royal Society of Medicine, Academic Press, London, 1978, pages 11-23.
[b]ROSZKOWSKI et al. - J. Pharmac. exp. Ther., (1971), 179, 114.

Five days subacute toxicity in rats per os

| Animals: 5 female rats for each group, average body weight: 150g. | | | | |
|---|---|---|---|---|
| Compound | Dose: mg/kg/die | % of dead animals | % of dead animals per day | Relative ratio to piroxicam | naproxen |
| Piroxicam | 20 | 0 | — | 1 | — |
|  | 30 | 40 | 6 | — | — |
| Naproxen | 50 | 0 | — | — | 1 |
|  | 100 | 20 | 5 | — | — |
| I-1 | 200[a] | 0 | — | 10 | 4 |
| I-2 | 200[a] | 0 | — | 10 | 4 |
| I-3 | 200[a] | 0 | — | 10 | 4 |
| I-4 | 100 | 0 | 0 | 5 | 2 |
|  | 200 | 20 | 4 | — | — |
| I-20 | 350[a] | 0 | — | 17 | 7 |
| I-21 | 350[a] | 0 | — | 17 | 7 |
| I-23 | 200[a] | 0 | — | 10 | 4 |
| I-24 | 200[a] | 0 | — | 10 | 4 |

[a]maximum tested dose.

Gastrolesive effect according to MANN and SACHDEV, Gastroenterology, 70, ASS/913, 1976. The test was modified by increasing the fast period to 70 hours and giving the total dose of substance in one single oral administration.

| Animals: 10 male rats for each group, average body weight: 150g. | | | | |
|---|---|---|---|---|
| Compound | Dose: mg/kg | Average number of lesions per animal | Relative potency to piroxicam | naproxen |
| Control | — | 0 | — | — |
| Piroxicam | 1 | 0 | 1 | — |
|  | 2.5 | 2.7 | — | — |
| Naproxen | 5 | 0 | — | 1 |
|  | 7.5 | 0.9 | — | — |
| I-1 | 100[a] | 0 | 100 | 20 |
| I-2 | 100[a] | 0 | 100 | 20 |
| I-3 | 100[a] | 0 | 100 | 20 |
| I-4 | 100[a] | 0 | 100 | 20 |
| I-20 | 100[a] | 0 | 100 | 20 |
| I-21 | 100[a] | 0 | 100 | 20 |
| I-23 | 100[a] | 0 | 100 | 20 |
| I-24 | 100[a] | 0 | 100 | 20 |

[a]maximum tested dose.

Antipyretic activity according to BURN et al., Biological Standardization, Oxford University Press, page 313, 1952.

| Animals: 6 female rats for each group, average body weight 200 g. | | | | |
|---|---|---|---|---|
| Compound | Dose: mg/g per os. | Reduction of the pyresis (in °C.) at hour 4 | Relative potency to piroxicam | naproxen |
| Piroxicam | 10 | 0.89 | 1 | — |
| Naproxen | 30 | 1.12 | — | 1 |
| I-1 | 50 | 0.86 | 1.0 | 0.8 |
|  | 100 | 1.44 | 1.6 | 1.3 |
| I-2 | 50 | 0.58 | 0.7 | 0.5 |
|  | 100 | 0.89 | 1.0 | 0.8 |
| I-3 | 50 | 0.77 | 0.9 | 0.7 |
|  | 100 | 1.08 | 1.2 | 1.0 |
| I-4 | 50 | 1.40 | 1.6 | 1.2 |
|  | 100 | 1.47 | 1.7 | 1.3 |
| I-20 | 50 | 0.45 | 0.5 | 0.4 |
|  | 100 | 0.75 | 0.8 | 0.7 |
| I-21 | 50 | 0.47 | 0.5 | 0.4 |
|  | 100 | 0.75 | 0.8 | 0.7 |
| I-23 | 50 | 1.20 | 1.3 | 1.1 |
|  | 100 | 1.42 | 1.6 | 1.3 |

-continued

| Animals: 6 female rats for each group, average body weight 200 g. | | | | |
|---|---|---|---|---|
| | | Reduction of the pyresis (in °C.) at hour 4 | Relative potency to | |
| Compound | Dose: mg/g per os. | | piroxicam | naproxen |
| I-24 | 50 | 0.81 | 0.9 | 0.7 |
| | 100 | 1.24 | 1.4 | 1.1 |

Analgesic activity according to HENDERSHOT et al., Jour. Pharm. Exp. Therm., 125, 237, 1959.

The test was modified by numbering the writhes only along the time interval from 5 to 15 minutes since the injection of phenylquinone. The injection was made 2 hours after the oral administration of the compound to be tested.

| Animals: 8 female mice for each group, average body weight: 25g | | | | |
|---|---|---|---|---|
| | | % inhibition of the writhes | Relative potency to | |
| Compound | Dose: mg/kg | | piroxicam | naproxen |
| Piroxicam | 10 | 46 | 1 | — |
| Naproxen | 30 | 33 | — | 1 |
| I-1 | 50 | 43 | 0.9 | 1.3 |
| | 100 | 72 | 1.6 | 2.2 |
| I-2 | 50 | 68 | 1.5 | 2.1 |
| | 100 | 92 | 2.0 | 2.8 |
| I-3 | 50 | 33 | 0.7 | 1.0 |
| | 100 | 60 | 1.3 | 1.8 |
| I-4 | 50 | 42 | 0.9 | 1.3 |
| | 100 | 59 | 1.3 | 1.8 |
| I-20 | 50 | 44 | 1.0 | 1.3 |
| | 100 | 72 | 1.6 | 2.2 |
| I-21 | 50 | 47 | 1.0 | 1.4 |
| | 100 | 65 | 1.4 | 2.0 |
| I-23 | 50 | 54 | 1.2 | 1.6 |
| | 100 | 79 | 1.7 | 2.4 |
| I-24 | 50 | 30 | 0.7 | 0.9 |
| | 100 | 47 | 1.0 | 1.4 |

Antiinflammatory activity according to WINTER et al., Proc. Soc. Exp. Biol. Med.; 111, 544; 1962.

The test was modified in that the injection of carrageenin and the administration of the compound by gastric gavage were carried out simultaneously and the paw edema was measured at the plethysmograph after 4 hours.

| Animals: 6 female rats for each group, average body weight: 150g | | | | |
|---|---|---|---|---|
| | | % inhibition of the edema after 4 hours | Relative potency to | |
| Compound | Dose mg/kg per os. | | piroxicam | naproxen |
| Piroxicam | 10 | 45 | 1 | — |
| Naproxen | 30 | 21 | — | 1 |
| I-1 | 50 | 10 | 0.2 | 0.5 |
| | 100 | 16 | 0.4 | 0.8 |
| I-2 | 50 | 12 | 0.3 | 0.6 |
| | 100 | 17 | 0.4 | 0.8 |
| I-3 | 50 | 9 | 0.2 | 0.4 |
| | 100 | 15 | 0.3 | 0.7 |
| I-4 | 50 | 36 | 0.8 | 1.7 |
| | 100 | 50 | 1.1 | 2.4 |
| I-20 | 50 | 15 | 0.3 | 0.7 |
| | 100 | 21 | 0.5 | 1.0 |
| I-21 | 50 | 12 | 0.3 | 0.6 |
| | 100 | 19 | 0.4 | 0.9 |
| I-23 | 50 | 27 | 0.6 | 1.3 |
| | 100 | 38 | 0.8 | 1.8 |
| I-24 | 50 | 38 | 0.8 | 1.8 |
| | 100 | 45 | 1.0 | 2.1 |

CONCLUSIONS (1) Toxicity (a) LD50: All the tested compounds according to the injection prove to be 2-10 times less toxic than piroxicam both in mice and in rats. With reference to naproxen, they prove to be sometimes less toxic in rats, whereas in mice they display about the same toxicity.

(b) 5 days subacute toxicity: in this test, the favorable values observed in rats under (a) are maintained or even increased (depending on the tested substance) both with respect to piroxicam and naproxen.

(c) Gastric ulcerogenicity: it results evident the almost complete absence of gastroulcerogenic effects displayed by the tested compounds according to the invention, whereas, in the same experiment, piroxicam and naproxen are endowed with considerable gastrolesive power.

(2) Activities

Taking into consideration the antiinflammatory, analgesic and antipyretic activities, it can be said that, when administered at 50 mg/kg, some of the compounds of the invention are more active than ulcerogenic dosage of piroxicam and naproxen; moreover, when administered at 100 mg/kg i.e., a certainly not gastrolesive dosage, all of the tested substances are more active than both reference compounds.

(3) Therapeutic forecasts

Considering the high safety margin deriving from the comparison between the toxicity and ulcerogenicity tests from one side and the pharmacological activity tests from the other side, the compounds of the invention are potential excellent analgesic, antipyretic and antiinflammatory or, more widely, antirheumatic drugs, which can be administered in the form of capsules for oral use containing from about 50 to about 100 mg of active ingredient, to be taken twice a day in single or divided dose, irrespective of whether the stomach is full or empty. The capsules contain an effective amount of the active ingredient in admixture with an almost equal amount of the usually employed, pharmaceutically acceptable carriers such as, for instance, lactose, talc and magnesium stearate.

I claim:

1. A 1,2-benzothiazino[3,4-d]pyrrole of formula I

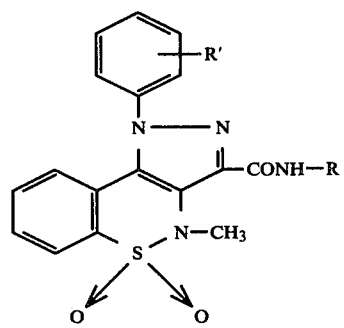

wherein R stands for a linear or branched ($C_{2-4}$) alkyl bearing a substituent of formula

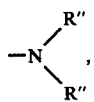

in which the R" radicals is the same or different and are hydrogen, $(C_{1-4})$ alkyl, $(C_{4-7})$ cycloalkyl or, taken together with the adjacent nitrogen atom, form a saturated, 5 to 7 membered heterocyclic ring containing from one to three heteroatoms independently selected from O, N and S; or R is the 1-ethyl-pyrrolidine-2-yl-methyl radical, and R' is a hydrogen, a halogen atom or a $(C_{1-4})$ alkyl radical.

2. A compound as defined in claim 1, wherein R is 2-dimethylaminoethyl, 2-diethylaminoethyl, 3-dimethylaminopropyl, 3-diethylaminopropyl, 3-morpholinopropyl, 3-cyclohexylaminopropyl or 1-ethyl-pyrrolidine-2-yl-methyl.

3. A compound as defined in claim 1, wherein R is 2-diethylaminoethyl, 3-dimethylaminopropyl, 3-morpholinopropyl, 3-cyclohexylaminopropyl or 1-ethyl-pyrrolidine-2-yl-methyl.

4. A compound as defined in claim 1, wherein R is 2-diethylaminoethyl and R' is hydrogen.

5. A compound as defined in claim 1, wherein R is 2-diethylaminoethyl and R' is a 4-methyl group.

6. A compound as defined in claim 1, wherein R is 2-diethylaminoethyl and R' is a 2-chloro group.

7. A compound as defined in claim 1, wherein R is 2-diethylaminoethyl and R' is a 3-chloro group.

8. A compound as defined in claim 1, wherein R is 2-diethylaminoethyl and R' is a 4-chloro group.

9. A compound as defined in claim 1, wherein R is 2-diethylaminoethyl and R' is a 3-fluoro group.

10. A compound as defined in claim 1, wherein R is 3-dimethylaminopropyl and R' is hydrogen.

11. A compound as defined in claim 1, wherein R is 3-dimethylaminopropyl and R' is a 4-methyl group.

12. A compound as defined in claim 1, wherein R is 3-dimethylaminopropyl and R' is a 2-chloro group.

13. A compound as defined in claim 1, wherein R is 3-dimethylaminopropyl and R' is a 3-chloro group.

14. A compound as defined in claim 1, wherein R is 3-dimethylaminopropyl and R' is a 3-fluoro group.

15. A compound as defined in claim 1, wherein R is 3-morpholinopropyl and R' is hydrogen.

16. A compound as defined in claim 1, wherein R is 3-morpholinopropyl and R' is a 4-methyl group.

17. A compound as defined in claim 1, wherein R is 3-morpholinopropyl and R' is a 2-chloro group.

18. A compound as defined in claim 1, wherein R is 3-morpholinopropyl and R' is a 3-chloro group.

19. A compound as defined in claim 1, wherein R is 3-morpholinopropyl and R' is a 4-chloro group.

20. A compound as defined in claim 1, wherein R is 3-morpholinopropyl and R' is a 3-fluoro group.

21. A compound as defined in claim 1, wherein R is cyclohexylaminopropyl and R' is hydrogen.

22. A compound as defined in claim 1, wherein R is cyclohexylaminopropyl and R' is a 4-methyl group.

23. A compound as defined in claim 1, wherein R is cyclohexylaminopropyl and R' is a 2-chloro group.

24. A compound as defined in claim 1, wherein R is cyclohexylaminopropyl and R' is a 3-chloro group.

25. A compound as defined in claim 1, wherein R is cyclohexylaminopropyl and R' is a 4-chloro group.

26. A compound as defined in claim 1, wherein R is cyclohexylaminopropyl and R' is a 3-fluoro group.

27. A compound as defined in claim 1, wherein R is 1-ethyl-pyrrolidine-2-yl-methyl and R' is hydrogen.

28. A compound as defined in claim 1, wherein R is 3-dimethylaminopropyl and R' is a 4-chloro group.

29. An antiinflammatory, antipyretic, antirheumatic and analgesic composition in unit dosage form, containing 50–100 mgs of a compound of formula I

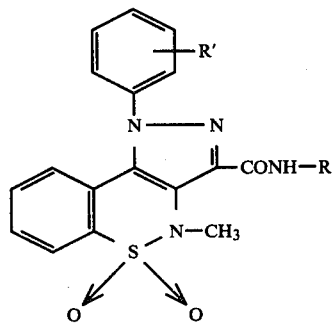

wherein R stands for a linear or branched $(C_{2-4})$ alkyl bearing a substituent of formula

in which the R" radicals are the same or different and are hydrogen, $(C_{1-4})$ alkyl, $(C_{4-7})$ cycloalkyl or, taken together with the adjacent nitrogen atom, are a saturated, 5 to 7 membered heterocyclic ring containing from one to three heteroatoms independently selected from O, N and S; or R is the 1-ethyl-pyrrolidine-2-yl-methyl radical, and R' is a hydrogen, a halogen atom or a $(C_{1-4})$ alkyl radical.

* * * * *